US006673401B2

(12) United States Patent
Black et al.

(10) Patent No.: US 6,673,401 B2
(45) Date of Patent: Jan. 6, 2004

(54) NANOPARTICLE STRUCTURES UTILIZING SYNTHETIC DNA LATTICES

(75) Inventors: Charles T. Black, White Plains, NY (US); Stephen M. Gates, Ossining, NY (US); Christopher B. Murray, New York, NY (US); Shouheng Sun, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 244 days.

(21) Appl. No.: 09/733,968

(22) Filed: Dec. 12, 2000

(65) Prior Publication Data

US 2002/0022111 A1 Feb. 21, 2002

Related U.S. Application Data

(62) Division of application No. 09/127,452, filed on Jul. 31, 1998, now Pat. No. 6,265,021.

(51) Int. Cl.[7] .......................... B32B 11/02; B05D 03/10
(52) U.S. Cl. ................ 428/34.1; 428/315.5; 428/315.7; 428/319.1; 428/694 B; 428/694 BA; 428/694 TC; 428/694 TP; 427/131; 536/23.1
(58) Field of Search ................................ 428/689, 34.1, 428/315.5, 315.7, 319.1, 694 B, 694 BA, 694 TP, 694 TC; 427/131, 282, 301, 307, 309, 333, 402

(56) References Cited

U.S. PATENT DOCUMENTS 4,802,951 A * 2/1989 Clark et al. ................. 156/630
5,583,211 A * 12/1996 Coassin et al. ............. 536/23.1
5,645,917 A * 7/1997 Ejiri et al. ................... 428/141
5,759,708 A * 6/1998 Tarasevich et al. ......... 428/689
6,107,038 A * 8/2000 Choudhary et al. ............ 435/6

\* cited by examiner

*Primary Examiner*—Harold Pyon
*Assistant Examiner*—Sow-Fun Hon
(74) *Attorney, Agent, or Firm*—Wan Yee Cheung, Esq.; McGinn & Gibb, PLLC

(57) ABSTRACT

A laminar structure upon a substrate is formed from a) a lattice layer comprising DNA (deoxyribonucleic acid) segments arranged to form cells of the lattice layer, and b), at least one nanoparticle being disposed within each cell of the lattice layer. The nanoparticles are preferably of substantially uniform diameter not exceeding 50 nanometers. A coating may be applied to adhere the the particles to the substrate and to maintain their substantially uniform spaced-apart relationship. The DNA lattice layer is fabricated using known automated synthetis methods, and is designed to contain specific nucleotide base sequences which cause the DNA to form an ordered array of openings, or lattice cells, by self-assembly. Self-assembly of the DNA lattice may be at an air-liquid interface, or in solution. A preferred embodiment is a magnetic storage medium in which the particles are magnetic particles with diameters in the range of 5–20 nm., the particles being organized in square information bits with each bit holding of 4, 9, 16, 25 etc. particles to produce areal information storage densities on the order of 1000 gigabits (one terabit) per square inch. The lattice of bits may be stabilized and protected by a deposited thin film, hard, abrasion-resistant coating.

18 Claims, 8 Drawing Sheets

NANOPARTICLE STRUCTURES UTILIZING SYNTHETIC DNA LATTICES

CROSS-REFERENCE TO RELATED APPLICATIONS

The present Application is a Divisional Application of U.S. patent application Ser. No. 09/127,452, filed on Jul. 31, 1998, which issued on Jul. 24, 2001 as U.S. Pat. No. 6,265,021 B1.

FIELD OF THE INVENTION

The present invention relates to fabrication of laminar layered structures in the form of ordered arrays or lattices of particles, preferably with lattice spacing on the scale of 10–100 nanometers (nm), known as the sub-micron length scale.

More particularly, the particles are characterized by substantially uniform diameters not exceeding 50 nanometers. Preferably, the particle diameters are in the 8–20 nm size range, and the distribution of particle diameters is <20% (the standard deviation of the distribution of particle diameters). Such particles can, for example, be produced in accordance with the methods described in the aforesaid application by C. Murray and S. Sun.

BACKGROUND OF THE INVENTION

To the present date, inexpensive and manufacturable patterning of magnetic media in the submicron size scale has been difficult to attain. The limitations of conventional lithographic patterning for dimensions below 0.1 micron (100 nm.) are well known, and are described in "Lithography for ULSI", by S. Okazaki, in a review paper (p. 18, vol. 2440, Proceedings of SPIE). Optical lithography with a light source in the deep ultra-violet ("DUV") is expected to serve in circuit and media fabrication for feature sizes no smaller than about 0.05 micron (50 nm). At present, there are no inexpensive methods for lateral patterning/texturing of solid substrates on a 5 to 50 nm scale.

Also previously, it was difficult or impossible to assemble ordered laminar structures or periodic arrays of particles or objects that are very small (5–20 nm, or 0.005–0.02 micron), and to reliably form such a laminar structure by a method that is simple and inexpensive. In addition, methods to adjust or tailor the lattice spacing in the size range 5–100 nm (0.005–0.1 micron) generally do not exist. There are numerous useful applications of such laminar structures. These include high density magnetic recording media, phased array radiation emitters, radiation sensor arrays, and patterns of electrical contacts/connections for high density interconnections between components. Such patterned electrical contacts are useful in the assembly of stacked integrated circuits.

An ideal method to make such laminar structures described above would have the following features:

1. The method is based on well known procedures and applies to patterning over useful areas (1 to 1,000 cm$^2$).
2. The method allows the spacing between nm scale particles or groupings of such particles to be easily adjusted.
3. The method scales up readily from the laboratory to a manufacturable process.
4. The size distribution, as measured by standard deviation, of the nm scale particles may reach about 20%, rather than the narrower size distribution (e.g. 10%) required by other patterning methods.

It is therefore an object of the present invention to provide such laminar structures as well as methods of fabrication which incorporate all of these features.

Accordingly, this invention proposes the use of a lattice layer, which is made of synthetic deoxyribonucleic acid (DNA), and is designed and fabricated by standard synthetic techniques, and forms by self-assembly of appropriately designed DNA segments. Self-assembly of the DNA lattice is performed in water solution, optionally at an air-liquid interface. The assembled lattice is then transferred onto a substrate surface where it is stabilized. This lattice provides lattice cells or sites which can hold one or more of nm-scale particles, which are thereby assembled into an ordered laminar structure that may have many useful applications.

Also disclosed herein is a chemical affinity/blocking method of assembly. In this method, the substrate surface and the particles are both coated with selected molecules which attract the particles to the substrate surface, and which also enable formation of covalent chemical links between the particles and the surface. The DNA lattice acts to "block" the attractive force between particles and the surface, leaving available lattice cells as attractive sites for particle binding and covalent linking only at the open regions in the DNA lattice layer.

A preferred embodiment provides an organized magnetic recording or storage medium with each bit consisting of about four suitable magnetic particles, and with a well controlled spacing between bits of 25 nm. Such a magnetic storage medium may have an areal information density of about $10^{12}$ bit/in$^2$ (1 terabit or Tbit/in$^2$.). Each bit occupies about 625 nm$^2$, and consists of about 4 magnetic particles (optionally crystalline) having a diameter of 8–10 nm. The particles may be ferromagnetic particles comprising a metal such as cobalt, iron, manganese, or nickel. A preferred composition is to alloy one or more of these metals with platinum, palladium or samarium. Alternatively, the particles are made of a ferromagnetic oxide, two examples being $BaFe_{12}O_{19}$ and $SrFe_{12}O_{19}$. Optionally, each magnetic particle bit is covered with a thin layer of a noble metal (silver, gold, platinum or palladium). A fabrication method for such a magnetic storage medium is also disclosed.

Moreover, a second embodiment having 9 magnetic particles/bit provides an information density of about $5 \times 10^{11}$ bit in$^2$ (0.5 Tbit in$^2$), and an area/bit of about 1,400 nm$^2$. Other embodiments with about 16 and 25 particles/bit are also described.

An alternative embodiment of the present invention permits an array of electrical connections between two different parts with each connection made by a metal particle (gold, for example) of diameter 10–50 nm with spacing between said metal particle connections on the scale of 10–50 nm. The metal particle connections are typically arranged in a square lattice pattern.

SUMMARY OF THE INVENTION

It is a purpose of the present invention to easily make laminar layered structures of particles (including but not restricted to crystalline ferromagnetic and semiconductor particles) having a substantially uniform diameter not exceeding 50 nm. It is a further purpose of the present invention to adjust, or tailor, the spacing between the particles in the aforesaid laminar structure within the 10–100 nm (0.01–0.1 micron) size range. Both of these two purposes allow fabrication of magnetic recording media, optically emmitting arrays, and parallel electrical connections with a very high areal density. It is still another object of this invention to stabilize said ordered arrays on a solid substrate, and when necessary to protect said arrays with a thin film overcoating.

The present invention provides a laminar layered structure of nanometer scale particles (the second lattice), with the lattice constant controlled by a coincident lattice layer of deoxyribonucleic acid (DNA). The particles typically have diameters (D) in the 5–20 nanometer (nm) range. The DNA lattice (first lattice) is fabricated using standard automated synthetic methods, and is designed to contain specific nucleotide base sequences, said sequences causing the DNA to form an ordered array of openings, or lattice sites, by self-assembly. Self-assembly of the DNA first lattice is at an air-liquid interface, or in solution.

A preferred embodiment is a magnetic recording or storage medium in which the particles are ferromagnetic particles with diameters in the range of 5–20 nm. and said particles are organized in square information bits with each bit consisting of 4, 9, 16, 25 (etc.) particles, and the lattice of bits is stabilized and protected by a deposited thin film hard coating. Such magnetic storage medium can attain areal information storage densities in the 0.1 to 1 terabit per square inch range.

Moreover, according to another embodiment, the invention can be utilized to create a laminar structure of nm-scale particles in selected patterns or regions of a substrate surface, while leaving the remaining regions free of said particles. The purpose is that selected patterns of the substrate can be made with customized properties by selective placement of the ordered arrays of nm-scale particles. To accomplish selective placement of said particles, an affinity coating (enabling the formation of chemical links between the particles and the substrate) on the substrate is patterned using lithographic methods. This coating is removed in selected regions, and left intact in the remaining regions. The pattern of the affinity coating may have any desired shape, either geometric or an arbitrary shape. Then during assembly (as shown in FIG. 5 and FIG. 7), the nm-scale particles adhere to the substrate only in the selected regions containing the intact affinity coating. The nm-scale particles do not adhere in the regions of the substrate where the affinity coating has been removed.

Accordingly, the present invention broadly provides a laminar layered structure comprising:

a) a substrate having a surface,
b) a lattice layer in the form of a lattice disposed upon said surface of said substrate, said lattice layer comprising DNA segments arranged to form cells of said lattice layer,
c) at least one particle disposed within each cell.

Preferably, particles within cells of the lattice layer have a substantially uniform diameter not exceeding 50 nanometers. For the purpose of particle diameters of the present invention, the term "substantially uniform" shall mean that the standard deviation of particle diameters should not exceed 20% of the mean particle diameter. Such tolerances of particle diameter are desireable to facilitate the the disposition of particles within cells of the lattice Preferably, the laminar layered structure further comprises d) an adherent coating disposed over the aforesaid lattice layer and over the aforesaid particles to maintain each particle within a cell of said lattice. Preferably, the adherent coating comprises abrasion-resistant material selected from the group consisting of diamond-like-carbon, amorphous carbon, amorphous silicon, aluminum oxide, and silicon oxide.

Especially for use in a magnetic storage medium, each cell has a diameter not exceeding 100 nanometers and the particles have a substantially uniform diameter not exceeding 20 nanometers. These particles may then comprise a magnetic material selected from the group consisting of elements Co, Fe, Ni, Mn, Sm, Nd, Pr, Pt, Gd, an intermetallic compound of the aforesaid elements, a binary alloy of said elements, a ternary alloy of said elements, an oxide of Fe further comprising at least one of said elements other than Fe, barium ferrite, and strontium ferrite. Moreover, each cell may optionally contain a plurality of said particles, where this plurality is the square of an integer.

According to other embodiments, each particle may comprise a material having a selected degree of electrical conductivity, and the particles may have a substantially uniform diameter not exceeding 50 nm. For example, the material may have a high degree of electrical conductivity for use of the laminar layered structure as an electrical contact layer for contacting a similar layer on a different substrate. Alternatively, the material may be a semiconductor material capable of emitting electromagnetic radiation for use of the laminar layered structure as a phased array emitter. According to another embodiment, the material may be a semiconductor material capable of sensing electromagnetic radiation for use in optical or other radiation detectors.

Moreover, to form a patterned layered structure, an affinity layer is disposed in a selected pattern over at least part of the surface of the substrate, the affinity layer being composed of an affinity material adapted to preferentially attract and retain the particles in the aforesaid selected pattern over the surface. Such an affinity material may preferably comprise bi-functional molecules having a group selected from tri-alkoxysilane and trichlorosilane at one end thereof and, at another end thereof, a group selected from carboxil acid and thiol.

In general, the affinity layer is formed by a layer of molecules which have two active chemical groups which should be selected to bind to the substrate and the nanopaticle surface thereby tethering the particles to the substrate surface. Affinity molecules can be expressed generally in the form X-R-Y where X and Y are the active head groups and R is a hydrocarbon or flourocarbon chain preferably containing 3–22 carbon atoms.

The functional groups X and Y are chosen from:

sulfonic acids R—SO$_2$OH sulfinic acids R—SOOH phosphinic acids R$_2$POOH phosphonic acids R—OPO(OH)$_2$ carboxylic acids R—COOH thiols R—SH trismethoxysilane R—Si(OCH$_3$)$_3$ trisethoxysilane R—Si(OCH$_2$CH$_3$)$_3$ trichlorosilane R—SiCl$_3$ In a given affinity molecule the chemical functional groups X and Y may be the same although they are generally not, because the substrate surface and the nanoparticle surface are generally comprised of different materials.

One example of an affinity layer is trismethoxysilylpropane thiol, which may be expressed as (CH$_3$O)$_3$Si—CH$_2$—CH$_2$—CH$_2$—SH, which selectively binds noble metal coated nanocrystals to silicon oxide surfaces.

The present invention further provides a method of forming a laminar layered structure upon a surface of a substrate comprising the steps of:

a) coating said substrate with an affinity coating,
b) preparing a solution (e.g. aqueous or CsCl) of a selected group of four DNA segments each formed from a base molecules of adenine (A), guanine (G), cytosine (C), and thymine (T), c) bringing said surface into contact with said solution to thereby apply a layer of said solution to said surface, d) drying said layer to leave a lattice layer of cells formed by DNA segments upon said surface, e) preparing a liquid dispersion of inorganic particles coated with an organic stabilizer material, said inorganic particles having a substantially uniform diameter not exceeding 50 nanometers.

f) applying said liquid dispersion to said surface of said substrate to cause at least one of said inorganic particles coated with said organic stabilizer material to adhere to said surface within each cell of said lattice layer, said particles being maintained in spaced-apart relationship upon said surface by said organic stabilizer material.

Moreover, it may be preferable to then remove the aforesaid organic stabilizer material, and depositing an adherent coating over said particles to maintain them in the aforesaid substantially uniformly spaced-apart relationship. Such removal of the organic stabilizer material may be carried out by evaporation using at least one of heating, dry etching, and vacuum.

In general, possible organic stabilizers for nanoparticles are long chain organic compounds which may be expressed in the form R-X where:

(1) R-a "tail group" which is either a straight or branched hydrocarbon or flourocarbon chain.

R-typically contains 8–22 carbon atoms (2) X-a "head group" which is a moiety (X) which provides specific chemical attachment to the nanoparticle surface. Active groups could be sulfinate (—$SO_2OH$), sulfonate (—SOOH), phosphinate (—POOH), phosphonate —OPO$(OH)_2$, carboxylate, and thiol.

Thus the stabilizers which result are: sulfonic acids

R—$SO_2OH$ sulfinic acids R—SOOH phosphinic acids $R_2POOH$ phosphonic acids R—OPO$(OH)_2$ carboxylic acids R—COOH thiols R—SH One specific choice of organic stabilizer material is oleic acid.

BRIEF DESCRIPTION OF THE DRAWINGS

The foregoing and other objects, aspects, and advantages will be better understood from the following description of the invention with reference to the drawings, in which.

DETAILED DESCRIPTION

Figure 1:
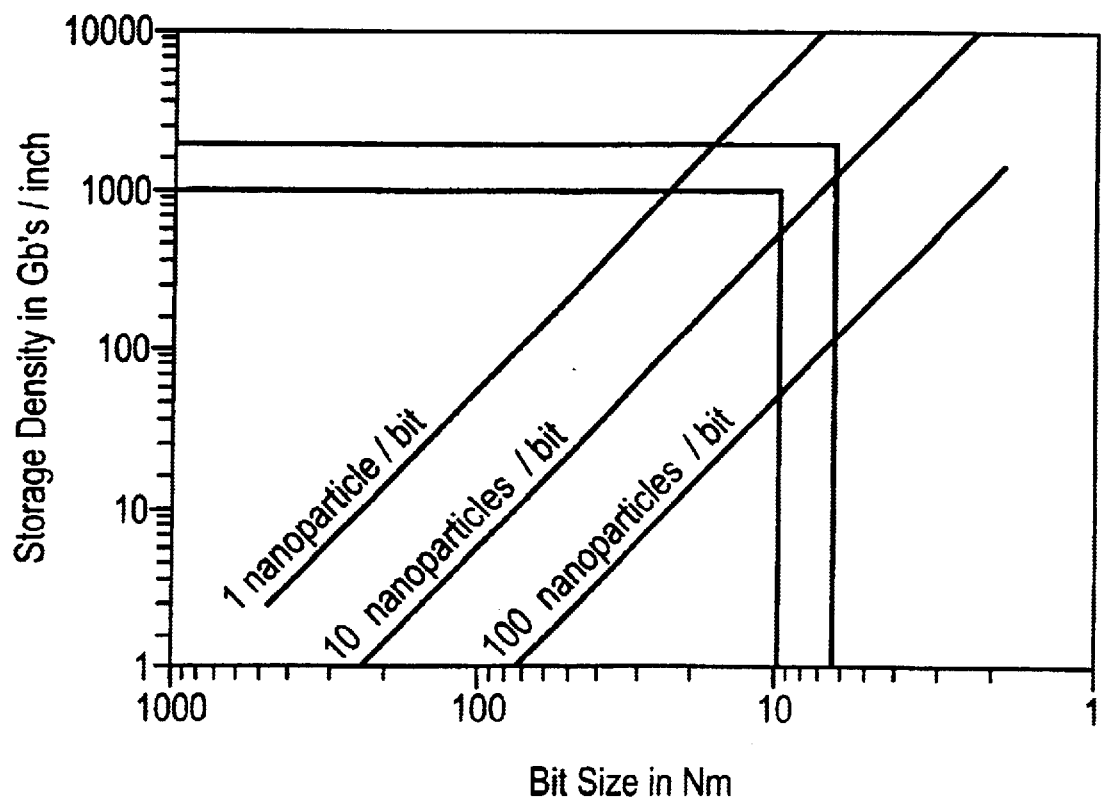
FIG. 1 is a plot of areal information storage density versus bit size.

FIG. 1 illustrates the main motivation for using the present invention, and is a plot of areal information density versus bit size. The density of information recording depends on the size of the bit. Density is expressed in Gbit $in^2$, where 1 Gbit=$10^9$ bits. Bit size (diameter of the bit) is expressed in nm., where 1 nm.=$10^{-7}$ cm.

Figure 2A:
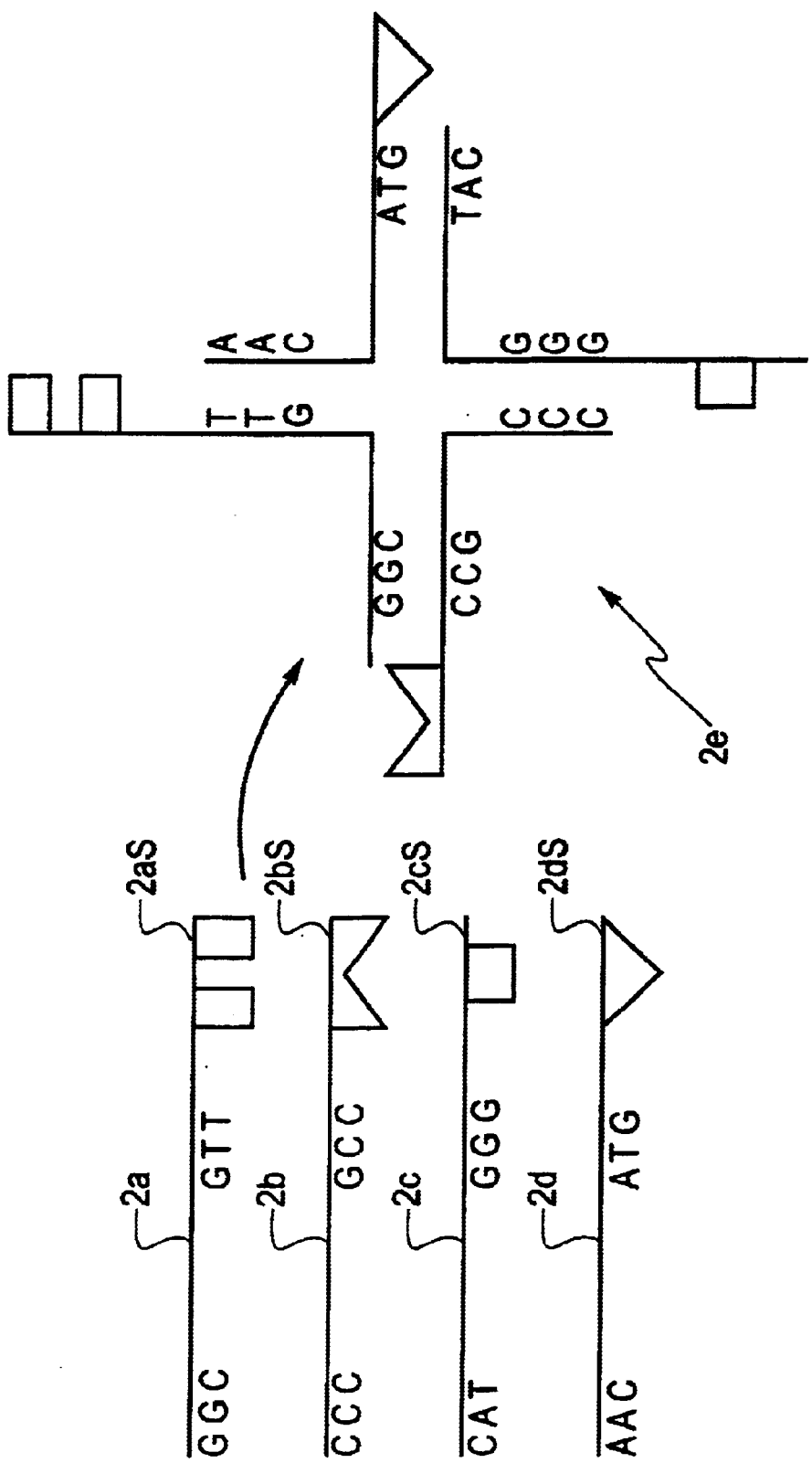
FIG. 2A is a schematic illustration of self-assembly of a DNA lattice structure element shown on the right side from four different DNA segments shown on the left side.
Figure 2B:
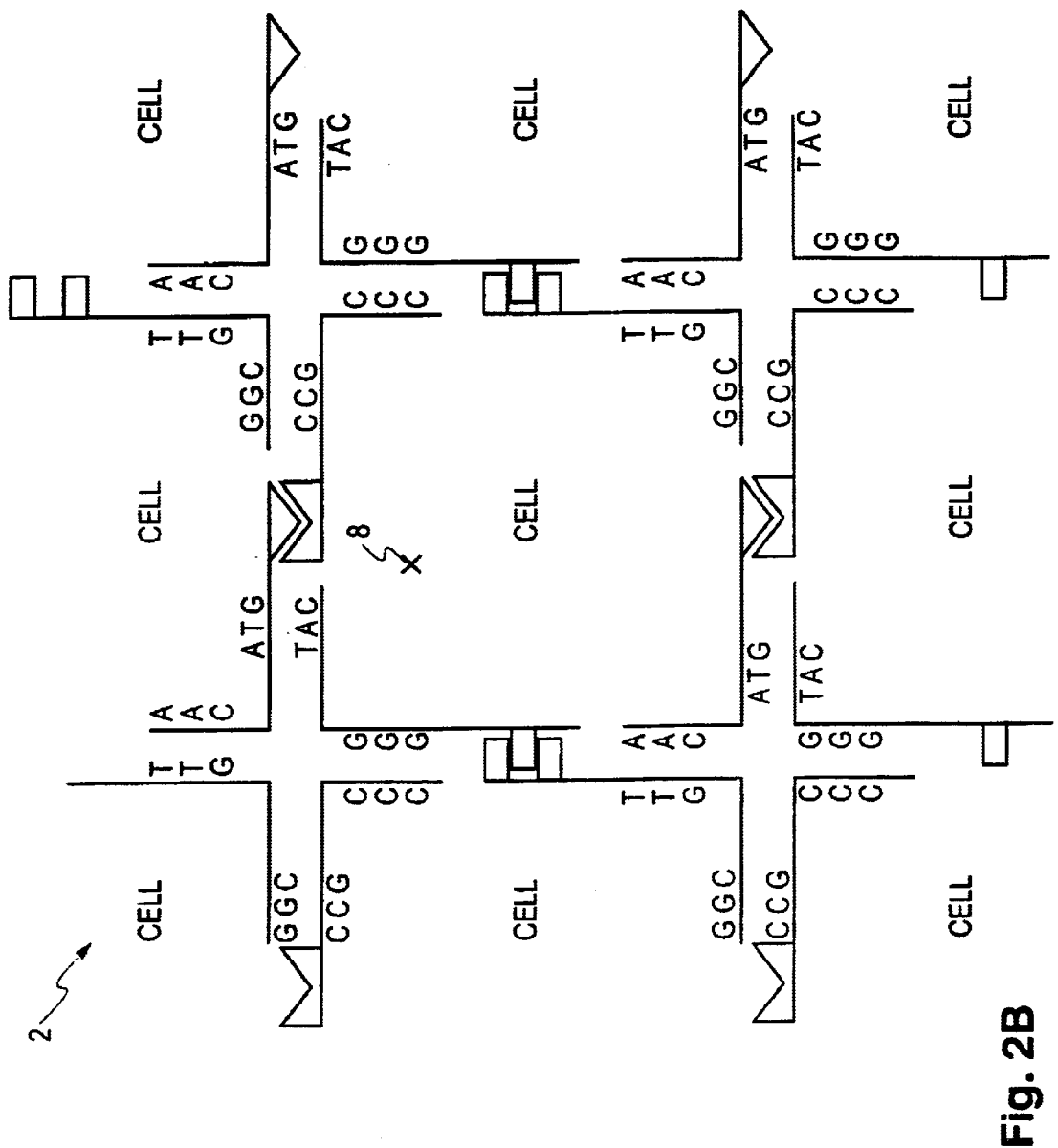
FIG. 2B is a schematic illustration of self-assembly of DNA lattice structure elements into a lattice layer.

FIGS. 2A and 2B show prior art methods described by N. C. Seeman in Accounts of Chemical Research, vol. 30 (1997), no. 9 page 357, which concern design of synthetic DNA segments.

FIG. 2A shows self-assembly of a synthetic DNA lattice structure element 2e from a pool comprised of 4 different synthetic DNA segments 2a, 2b, 2c, and 2d. Each DNA segment in the pool is designed and synthesized and mixed in solution. Each designed DNA segment (e.g. 2b) must have a "Sticky End" (a specific nucleotide base sequence) which is represented by a geometric shape (e.g. 2bS) in FIG. 2A. In DNA synthesis, as is known, the base C binds only to G, and the base A binds only to T. Each designed segment must have a chosen nucleotide base sequence that selectively binds only 1 other designed DNA segment in the pool. In FIG. 2A, the chosen base sequence is represented by a triplet of bases chosen from A (adenine), G (guanine), C (cytosine), and T (thymine), to illustrate the method. When fabricating the structures of the present invention, the chosen segments should contain more than three bases. Further, each DNA segment has a length, designated the Monomer Arm Length (M), which is simply a nucleotide base sequence (e.g. GTT) having a selected length (e.g. 3). Preferably, M consists of an integral number of half-turns of the DNA helix. The segments are made by standard DNA synthetic methods.

FIG. 2B shows self-assembly of the DNA lattice 2 from the designed DNA segments 2a, 2b, 2c, and 2d. The Sticky Ends bind only to the complementary Sticky End. The chosen base sequences (triplets in FIGS. 2A and 2B) bind only to the complementary base sequence. The DNA self-assembles to form an ordered, square planar, lattice consisting of DNA double-helix strands and openings, or lattice cells 8. The ordered DNA lattice is formed by self-assembly in solution, or at an air water interface. Different symmetries such as trigonal symmetry are also possible for the DNA lattice. The lattice array is then transferred to a solid support ("substrate") as a lattice layer thereon.

One convenient method to transfer the DNA lattice from aqueous solution onto the substrate is the "Langmuir-Blodgett Technique", which is commonly used to transfer a self-assembled monolayer of specialized molecules from the liquid phase to the surface of a substrate. The molecules are specialized because there are 2 distinct ends of each molecule: a hydrophobic (water-hating) end, and a hydrophilic (water-loving) end. Thus, the molecules form an ordered monolayer floating on water (the liquid phase). The "Langmuir-Blodgett Technique" consists of vertically drawing the substrate through the monolayer/water interface to transfer said monolayer onto the substrate, and this technique also involves controlling and adjusting variables including the temperature, surface pressure, and rate of drawing the substrate. Details of the "Langmuir-Blodgett Technique" are described in detail by M. C. Petty in chapters 3 and 4 of the book *Langmuir-Blodgett Films, an Introduction,* (copyright 1996 by Cambridge Univ. Press, NY. ISBN #0 521 41396 6 or #0 521 42450 X). The transfer method of the present invention consists of floating the self-assembled DNA lattice on top of an aqueous solution, and then proceeding with the Langmuir-Blodgett transfer onto a substrate surface.

Figure 3:
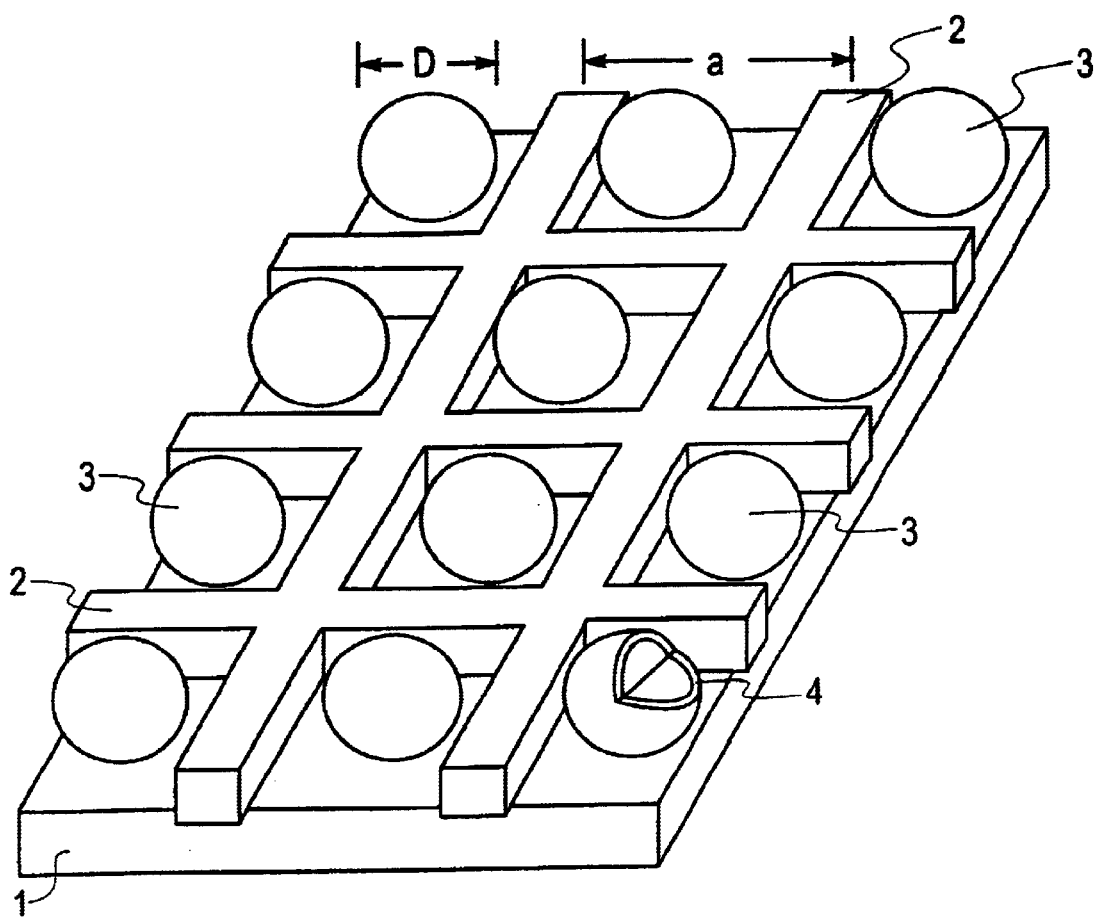
FIG. 3 is a schematic perspective view of a laminar layered structure in accordance with the present invention, wherein a single particle is disposed within each cell of the lattice layer.

FIG. 3 shows the DNA lattice layer 2 after transfer to the surface of substrate 1, and shows the particles 3, each preferably having a layer 4 of an organic stabilizer material (e.g. oleic acid) as disclosed in copending application YO8-98-218. The lattice constant, a, equals 2M, where M is the Monomer Arm Length. FIG. 3 shows a simple example wherein the size of the DNA lattice openings is slightly larger than the diameter, D, of the nm-scale particles. This example is useful in fabrication of an alternative embodiment, namely the array of electrical connections between 2 parts with each connection made by metal particle of diameter 10–500 nm with spacing between said metal particle connections on the scale of 10–500 nm. In the illustrated embodiment of FIG. 3, no overcoat is used.

Figure 4:
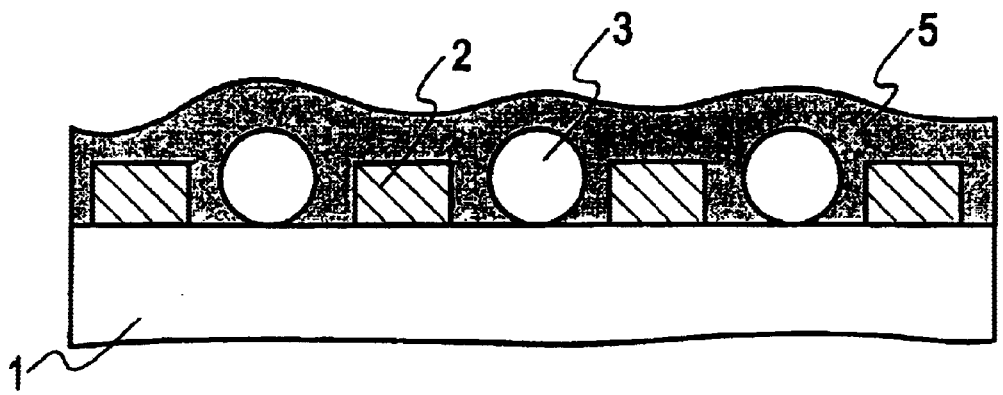
FIG. 4 is a sectional view of the laminar layered structure of FIG. 3, and further shows an adherent coating disposed over the DNA lattice layer and the particles.

FIG. 4 illustrates addition of a protective abrasion-resistant coating 5 over the DNA lattice layer 2 and the particles 3, which are of a magnetic material. The coating 5 is required in order to use the resultant laminar layered structure (comprising substrate 1, DNA lattice 2, and particles 3) as a magnetic recording or storage medium, which involves potential abrasion from a read/write head, and the like. Of course, the particles may comprise any suitable magnetic material, such as a material selected from the group consisting of elements Co, Fe, Ni, Mn, Sm, Nd, Pr, Pt, Gd, an intermetallic compound of the aforesaid elements, a binary alloy of said elements, a ternary alloy of said elements, an oxide of Fe further comprising at least one of said elements other than Fe, barium ferrite, and strontium ferrite.

Figure 5:
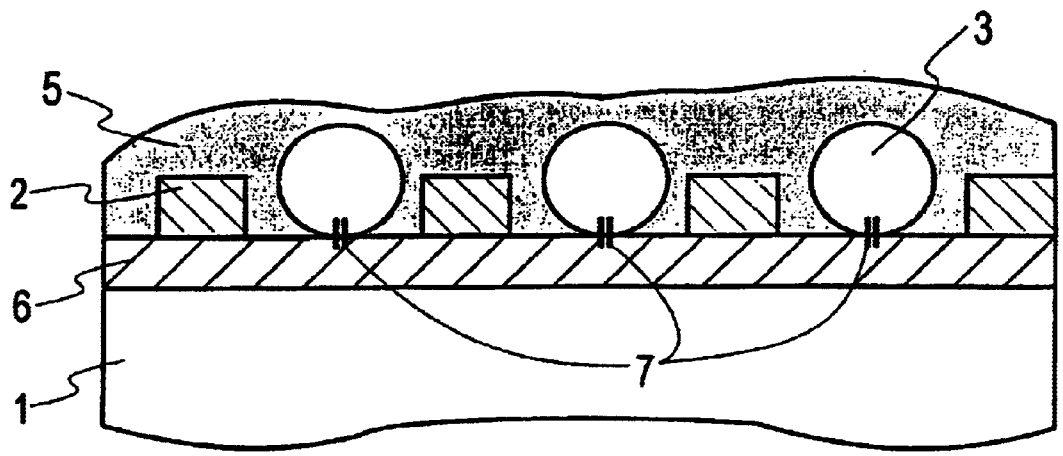
FIG. 5 is a sectional view of a laminar layered structure according to the invention, wherein layers of affinity material are used to select locations on a substrate to which particles can adhere.

FIG. 5 shows a chemical affinity/blocking method for making the laminar layered structures of the present invention. Before other steps, the surface of substrate 1 is coated with a suitable affinity coating 6 to create chemical links between the particles 3 and the surface of substrate 1. On the substrate 1, the affinity coating 6 may, for example, comprise bi-functional molecules with two distinct ends: at 1 end is a tri-alkoxysilane group (trimethoxy- and triethoxy-silanes being preferred), which will link covalently to an SiO2 or metal oxide surface. A glass substrate, or Si wafer coated with SiO2, is used. At the other end is a carboxilic acid or thiol group. These groups form strong carboxilate or thiolate linkages, respectively, with the metal magnetic particles. Between the two ends is a hydrocarbon chain.

In general, the affinity layer is formed by a layer of molecules which have two active chemical groups which should be selected to bind to the substrate and the nanopaticle surface thereby tethering the particles to the substrate surface.

Affinity molecules can be expressed generally in the form X-R-Y where X and Y are the active head groups and R is a hydrocarbon or flourocarbon chain preferably containing 3–22 carbon atoms.

The functional groups X and Y are chosen from:
sulfonic acids R—$SO_2OH$
sulfinic acids R—SOOH
phosphinic acids $R_2POOH$
phosphonic acids R—$OPO(OH)_2$
carboxylic acids R—COOH
thiols R—SH
trismethoxysilane R—$Si(OCH_3)_3$
trisethoxysilane R—$Si(OCH_2CH_3)_3$
trichlorosilane R—$SiCl_3$ In a given affinity molecule the chemical functional groups X and Y may be the same although they are generally not, because the substrate surface and the nanoparticle surface are generally comprised of different materials.

One example of an affinity layer is trismethoxysilylpropane thiol, which may be expressed as $(CH_3O)_3Si$—$CH_2$—$CH_2$—$CH_2$—SH, which selectively binds noble metal coated nanocrystals to silicon oxide surfaces.

The DNA lattice 2 acts to "block" the formation of covalent links 7, leaving open pockets or cells at the openings in the square lattice 2. Covalent chemical links bind the particles to the surface in the open areas.

It is sometimes desirable to create a laminar layered structure of nm-scale particles in selected regions of a substrate surface, while leaving the remaining regions free of said particles. The purpose is that selected regions of the substrate can be made with customized properties by selective placement of the ordered arrays of nm-scale particles. To accomplish selective placement of said particles, the affinity coating 6 (enabling the formation of chemical links between the particles 3 and the substrate 1) on the substrate is patterned using known lithographic methods. The coating 6 is removed in selected regions, and left intact in the remaining regions. The pattern of the affinity coating 6 may have any shape, either geometric or an arbitrary shape. Then, during assembly (as shown in FIG. 5 and in FIG. 7), the nm-scale particles 3 coated with affinity coating 6 adhere to the substrate only in the selected regions of substrate 1 that retain an intact affinity coating 6. The nm-scale particles 3 do not adhere in the regions of the substrate 1 where the affinity coating 6 was removed.

Figure 6:
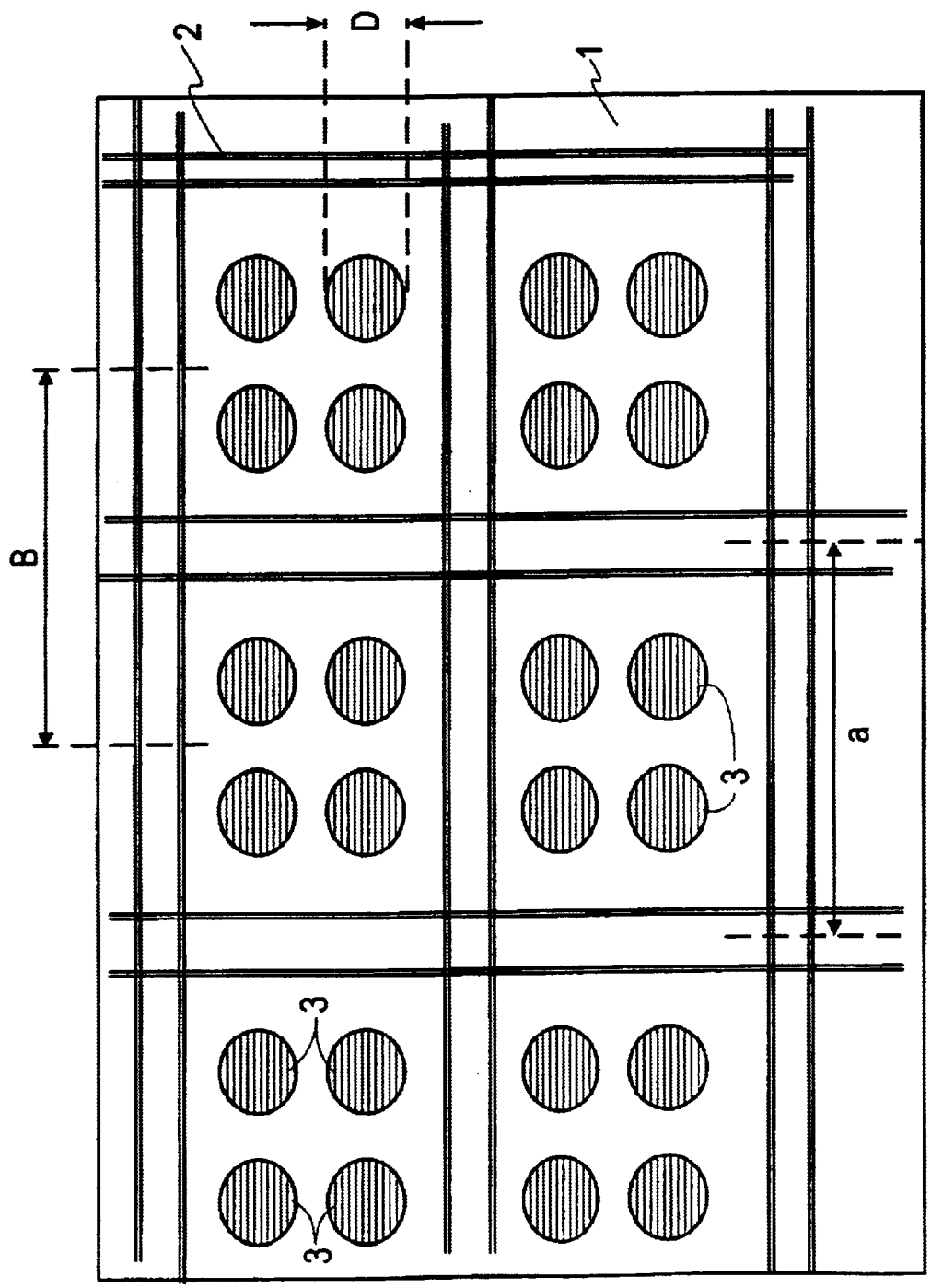
FIG. 6 is a plan view of an inventive embodiment in which four particles are disposed in each cell of the lattice layer.

FIG. 6 shows that the structures and methods shown in FIGS. 3–5 may be applied to make a magnetic storage medium with $N^2$ particles within each lattice site of the first lattice, where N=2, 3, 4, 5, etc. FIG. 6 is a plan view of a magnetic recording medium in which the cell area of each information bit is about 600–700 $nm^2$ and each bit consists of about four (4) magnetic particles, and the information areal density is about about 0.8–0.9=$10^{12}$ bit/$in^2$(0.8–0.9 Tbit/$in^2$.). The lattice constant a of the lattice layer 2 is also the spacing between bits, B, which is about 25–27 nm. The diameter, D, of each magnetic particle is 8 nm in the FIG. 6 (in other embodiments, diameter may preferably be in the range 8–20 nm. As will be understood, the horizontal and vertical lines represent the DNA lattice 2.

Each ferromagnetic particle is made of a metal such as cobalt, iron, manganese, or nickel. A preferred composition is to alloy 1 or more of said metals with platinum, palladium or samarium. Alternatively, the bits are made of a ferromagnetic oxide, two examples being $BaFe_{12}O_{19}$ and $SrFe_{12}O_{19}$. Optionally, each ferromagnetic particle may be covered with a thin layer of a noble metal (silver, gold, platinum or palladium). The diameter of each magnetic particle can be in the range 8–20 nm, and is preferably 8–12 nm.

Alternatively, if the cell area of each information bit is increased to about 1,400–1,600 $nm^2$ (for a lattice constant or bit spacing of about 38–40 nm) and each bit consists of about 9 ferromagnetic particles, then the information areal density would be about 0.4–0.5×$10^{12}$ bit/$in^2$ (0.4–0.5 Tbit/$in^2$).

Although not illustrated, it will be understood that other useful embodiments of this invention can be made using longer synthetic DNA sequences, resulting in larger lattice spacings, and placing 16 or 25 (or even larger numbers) of ferromagnetic particles in each information bit. For example, with 16 particles in each bit the area of each bit is about 2,000–2,500 $nm^2$ and the information areal density is about $0.27 \times 10^{12}$ bit $in^2$ (0.27 Tbit/$in^2$.). With 25 particles in each bit, the area of each bit is reduced to about 5,000–6,000 $nm^2$ and the information areal density is further reduced to about $0.13 \times 10^{12}$ bit/$in^2$ (0.13 Tbit/$in^2$).

It is also understood that the number of particles/bit as specified above is subject to variation from bit to bit due to errors in the fabrication method. The exact variation in number of particles/bit that is acceptable may be determined by the magnetic recording and sensing head that is used. For example, for 4-particle bit density (FIG. 6), the variation may be + or –1 or 2 particles, while for 9-particle bit density the acceptable variation may be + or –3 or 4 particles. When the number of particles/bit is larger (16 or 25), still larger variations may be acceptable.

FIGS. 7A, 7B, 7C, 7D, and 7E shows the steps in the general fabrication method of a preferred magnetic storage medium embodiment of this invention.

Figure 7A:
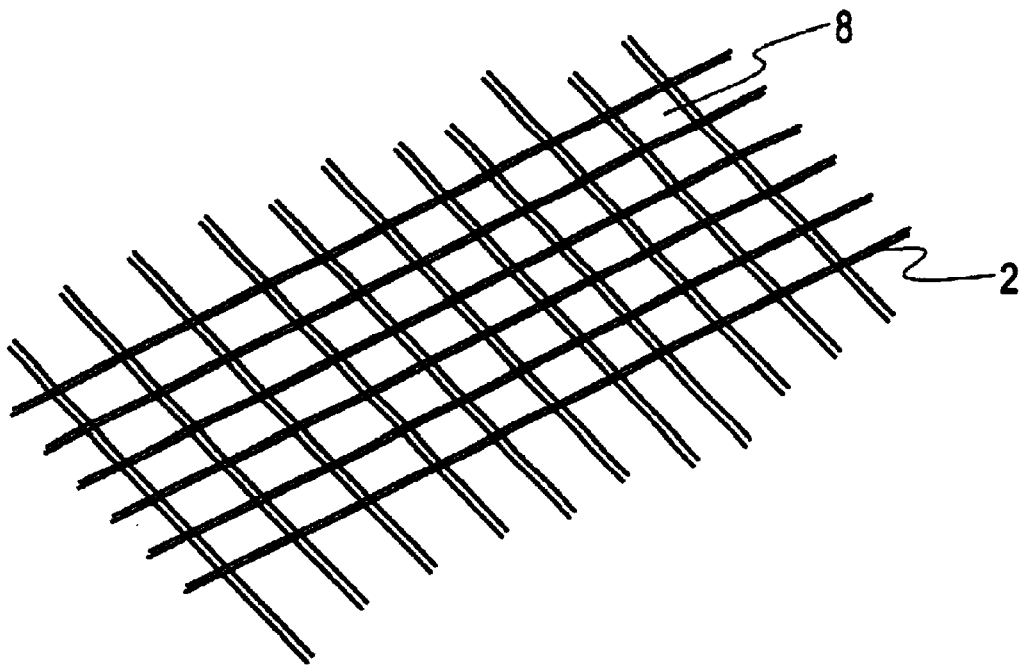
FIGS. 7A, 7B, 7C, 7D, and 7E are schematic views that illustrate Steps 1, 2, 3, 4, and 5, respectively, of a method of forming laminated layered structures according to the invention.

In FIG. 7A, Step 1 is the self-assembly in a water based solution of the DNA lattice 2. The specifically designed synthetic DNA sequence segments are placed in a buffered aqueous solution. Optionally, a concentrated solution of CsCl (with a high density) may be used to float the assembled DNA lattice 2.

Figure 7B:
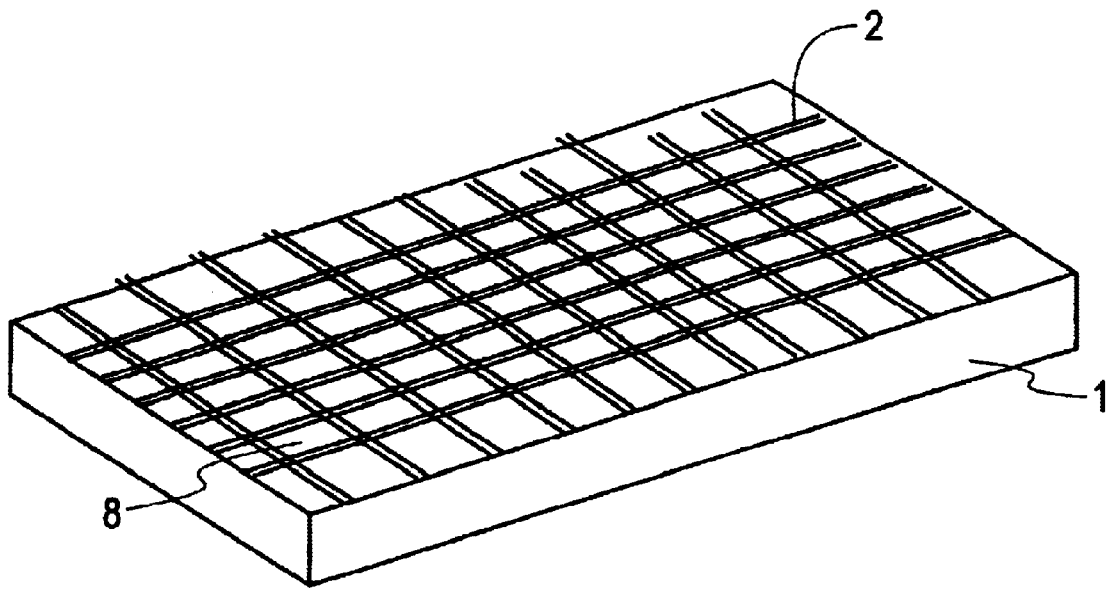

After the DNA self-assembles into the desired lattice, Step 2, the transfer onto a solid substrate, is performed as generally depicted in FIG. 7B. Step 2 may be performed, for example, using a Langmuir Blodgett film method and slowly pulling the substrate from the aqueous solution containing the DNA as described in detail in chapters 3 and 4 of reference 3 by M. C. Petty. Another method is to coat the substrate with a thin film of the aqueous solution containing the DNA (provided the thin film is uniform in thickness), followed by slow drying (evaporation of the water solvent). Spin coating may be used to form said uniform film of the DNA solution. In FIG. 7B, the DNA lattice has been stabilized by slow drying and is now firmly contacting the solid surface of substrate 1.

Figure 7C:
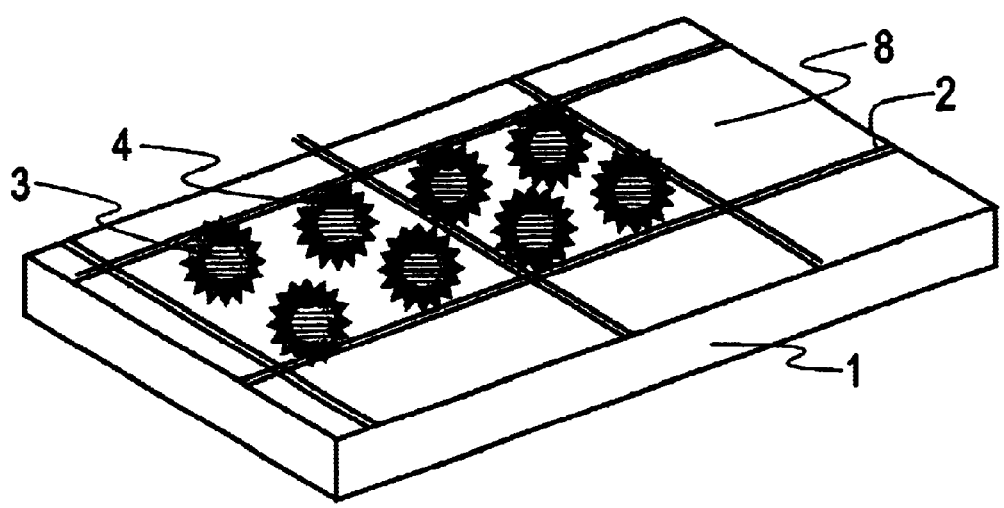

In Step 3, as depicted in FIG. 7C, substrate 1 is immersed in a solution of a hydrocarbon solvent containing ferromagnetic (e.g. Co) particles 3. The particles are soluble in this solvent because of their organic stabilizer coating 4 (e.g. oleic acid). Generally, the organic stabilizer material may comprise a long chain organic compound of the form R-X, where R is a member selected from the group consisting of 1) a hydrocarbon chain in straight or branched formation, said hydrocarbon chain comprising 6 to 22 carbon atoms, and 2) a fluorocarbon chain in straight or branched formation, said fluorocarbon chain comprising 6 to 22 carbon atoms, and where X is selected from carboxylic acid, phosphonic acid, phosphinic acid, sulfonic acid, sulfinic acids, and thiol. One specific choice of organic stabilizer material is oleic acid.

The DNA lattice 2 is insoluble in a hydrocarbon solvent. An attractive interaction, or affinity, between the organic stabilizer particle coating 4 and the substrate surface 1 attracts the particles to surface 1 in the regions of the surface 1 that are open or exposed. Said regions are the square openings or cells 8 in the DNA lattice 2. The DNA strands block particles from binding to the remaining area. This "blocked" area provides a non-ferromagnetic "border" surrounding each bit.

Figure 7D:
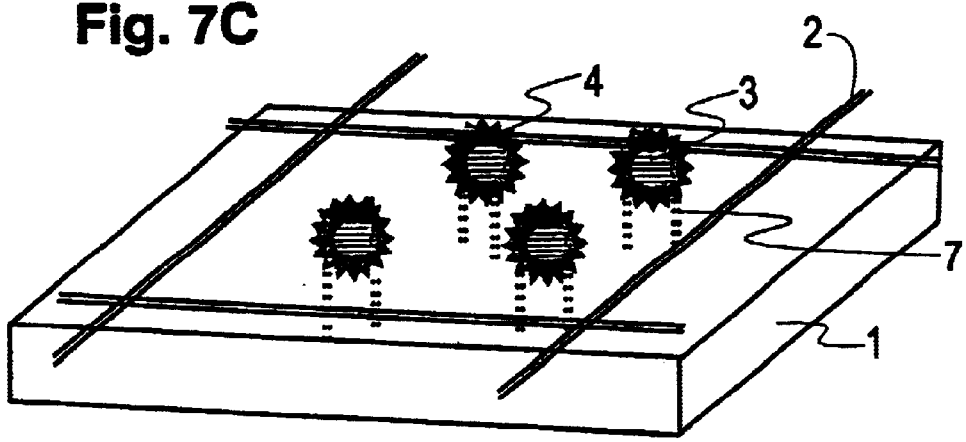

In Step 4 of FIG. 7D, the formation of covalent links 7 between the organic coat 6 of each ferromagnetic particle 3 and the substrate 1 is shown. Specifically, the covalent links 7 are formed between an affinity coating which may preferably have been pre-applied on the substrate 1 (bifunctional molecules with 2 distinct ends as described above in reference to FIG. 5) and the particles 3. At one end of such an affinity coating 6, a trimethoxy- or triethoxy-silane group forms covalent bonds to the glass or SiO2 substrate 1. At the other end is a carboxilic acid group which forms a stable carboxylate linkage to the Co particles 3.

Figure 7E:
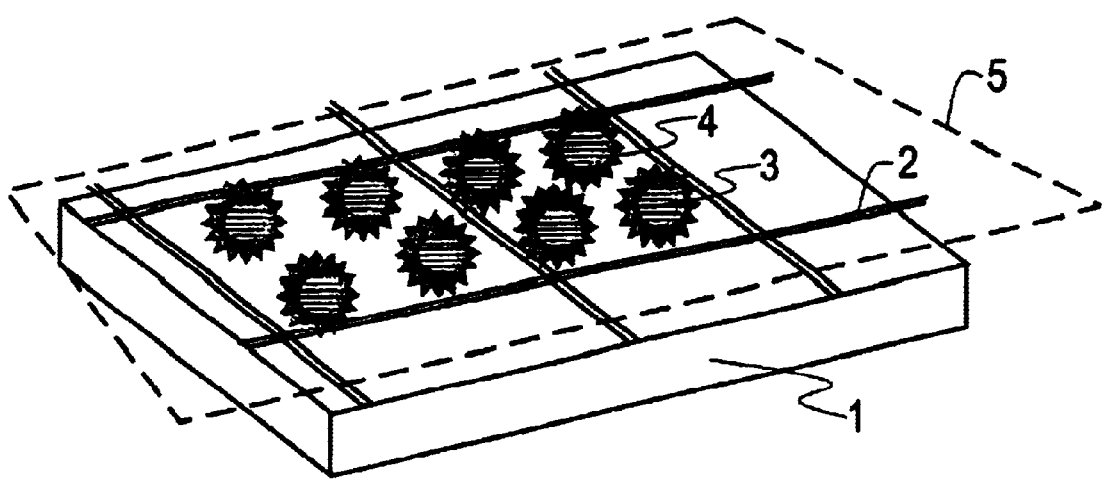

In Step 5 of FIG. 7E, the substrate 1 containing the covalently linked particles 3 is placed in a suitable deposition tool (for example a plasma enhanced chemical vapor deposition, PE CVD, tool) and a hard protective coating 5 is deposited. Coating 5 may typically be amorphous carbon. Other suitable coatings are diamond-like carbon, aluminum oxide, $SiO_2$, SiNitride, and other hard, scratch resistant, protective coatings. The thickness of coating 5 may be at least 10 nm and preferably 100 to 500 nm.

While the present invention has been described with reference to preferred embodiments thereof in order to facilitate a better understanding of the invention, those skilled in the art will recognize that the invention can be embodied in various ways without departing from the scope and spirit of the invention as set forth in the appended claims.

What is claimed is:

1. A laminar layered structure comprising:

a substrate having a surface;

a layer of synthetic DNA segments assembled on a substrate to produce a 2-dimensional crystal with a regular cellular structure for allowing colloidal particles to contact and adhere to the substrate; and an affinity layer disposed over at least part of said surface of said substrate; and a protective coating Conned over said layer of synthetic DNA segments, said particles and said affinity layer, wherein said synthetic DNA segments are produced with sequences permitting formation of a 2-dimensional lattice having a lattice spacing of less than 50 nm, wherein said colloidal particles are produced by solution phase synthesis and have diameters in a range of below 20 nm uniform in size to better than 10% in diameter, and wherein said particles comprise a magnetic material selected from the group consisting of elements Co, Fe, Ni, Mn, Sm, Nd, Pr, Pt, Gd, an intermetallic compound of the aforesaid elements, a binary alloy of said elements, a ternary alloy of said elements, an oxide of Fe further comprising at least one of said elements other than Fe, barium ferrite, and strontium ferrite, and wherein said affinity layer comprises a molecule comprises a first functional group for binding said affinity layer to said substrate, and a second functional group for binding said affinity layer to said at least one particle.

2. A laminar layered structure as set forth in claim 1, wherein each cell formed by the synthetic DNA lattice contains a plurality of particles, and wherein a number of particles per cell is an integer predetermined based on the DNA lattice cell size and particle size.

3. A laminar layered structure comprising:

a substrate having a surface;

a layer of synthetic DNA segments assembled on a substrate to produce a 2-dimensional crystal wit a regular cellular structure for allowing colloidal particles to contact and adhere to the substrate;

an affinity layer disposed over at least part of said surface of said substrate; and a protective coating formed over said layer of synthetic DNA segments, said particles and said affinity layer, wherein said synthetic DNA segments are produced with sequences permitting formation of a 2-dimensional lattice having a lattice spacing of less than 50 nm, wherein said colloidal particles are produced by solution phase synthesis and have diameters in a range of below 20 nm uniform in size to better than 10% in diameter, and wherein said particles comprise a magnetic material selected from the group consisting of elements Co, Fe, Ni, Mn, Sm, Nd, Pr, Pt, Gd, an intermetallic compound of the aforesaid elements, a binary alloy of said elements, ternary alloy of said elements, an oxide of Fe further comprising at least one of said elements other than Fe, barium ferrite, and strontium ferrite, wherein each particle comprises a material having a selected degree of electrical conductivity, and wherein said affinity layer comprises a molecule comprises a first functional group for binding said affinity layer to said substrate, and a second functional group for binding said affinity layer to said at least one particle.

4. A laminar layered structure as set forth in claim 1, wherein said affinity material is comprised of bi-functional molecules of the form X-R-Y, wherein R is selected from hydrocarbon and fluorocarbon chains of between 3 end 22 carbon atoms, and X and Y selected from:

sulfonic acids R—SO$_2$OH sulfinic acids R—SOOH phosphinic acids R$_2$POOH phosphonic acids R—OPO(OH)$_2$ carboxylic acids R—COOH thiols R—SH trismethoxysilane R—Si(OCH$_3$)$_3$ trisethoxysilane R—Si(OCH$_2$CH$_3$)$_3$ trichlorosilane R—SiCl$_3$.

5. A laminar layered structure comprising:

an affinity layer formed on at least a portion of a surface of a substrate;

a lattice-shaped layer of synthetic DNA segments formed on said affinity layer, said lattice-shaped layer comprising a plurality of cells;

at least one particle disposed within a cell of said plurality of cells; and a protective coating formed over said lattice-shaped layer, said at least one particle and said affinity layer, wherein said affinity layer comprises a molecule comprises a first functional group for binding said affinity layer to said substrate, and a second functional group for binding said affinity layer to said at least one particle.

6. The laminar layered structure as set forth in claim 5, wherein said substrate comprises silicon dioxide, said particle comprises a noble metal coated nanocrystal, said molecule comprises propane, said first functional group comprises a trimethoxysilyl group, and said second functional group comprises a thiol group.

7. The laminar layered structure as set forth in claim 5, wherein said first functional group comprises a tri-alkoxysilane group.

8. The laminar layered structure as set forth in claim 5, wherein said second functional group comprises one oh carboxylic acid and a thiol group.

9. The laminar layered structure as set forth in claim 5, wherein said molecule comprises one hydrocarbon and fluorocarbon chain between said first functional group and said second functional group.

10. The laminar layered structure as set forth in claim 5, wherein first functional group comprises at least one of a tri-methoxysilane group, a tri-ethoxysilane group, and a tri-chlorosilane group.

11. The laminar layered structure as set forth in claim 5, wherein said second functional group comprises at least one of a sulfonic acid group, a sulfinic acid group, a phosphinic acid group, a phosphonic acid group, a carboxylic acid group, and a thiol group.

12. The laminar layered structure as set forth in claim 5, wherein said cell has a diameter less than or equal to 100 nanometers, and said particle has a diameter less than or equal to 50 nanometers.

13. The laminar layered structure as set forth in claim 5, wherein said at least one particle comprises a noble metal coated particle.

14. The laminar layered structure as set forth in claim 5, wherein said at least one particle comprises at least one magnetic particle.

15. The laminar layered structure as set forth in claim 5, wherein said magnetic particle comprises at least one of Co, Fe, Ni, Mn, Sm, Nd, Pr, Pt, Gd, an intermetallic compound of the aforesaid elements, a binary alloy of said elements, a ternary alloy of said elements, an oxide of Fe further comprising at least one of said elements other than Fe, barium ferrite, and strontium ferrite.

16. The laminar layered structure as set forth in claim 5, wherein said at least one particle comprises an electrically conductive particle.

17. The laminar layered structure as set forth in claim 5, wherein said at least one particle comprises a semiconductor particle.

18. The laminar layered structure as set forth in claim 5, wherein said affinity layer is selectively formed on a predetermined portion of said surface of said substrate, so that said at least one particle is disposed at said predetermined portion.

* * * * *